US010106860B2

(12) United States Patent
Yoo et al.

(10) Patent No.: US 10,106,860 B2
(45) Date of Patent: Oct. 23, 2018

(54) SIMULTANEOUS DIAGNOSIS KIT FOR A DISEASE DUE TO A RESPIRATORY VIRUS

(75) Inventors: Eun Joo Yoo, Daejeon (KR); Young Suk Park, Daejeon (KR); Ji Eun Heo, Daejeon (KR); Jin Seok Kang, Daejeon (KR)

(73) Assignee: LG Chem, LTD., Seoul (KR)

( * ) Notice: Subject to any disclaimer, the term of this patent is extended or adjusted under 35 U.S.C. 154(b) by 149 days.

(21) Appl. No.: 14/000,153

(22) PCT Filed: Feb. 20, 2012

(86) PCT No.: PCT/KR2012/001262
§ 371 (c)(1),
(2), (4) Date: Oct. 28, 2013

(87) PCT Pub. No.: WO2012/112012
PCT Pub. Date: Aug. 23, 2012

(65) Prior Publication Data
US 2014/0127671 A1    May 8, 2014

(30) Foreign Application Priority Data
Feb. 18, 2011  (KR) .................. 10-2011-0014807

(51) Int. Cl.
*C12Q 1/68* (2018.01)
*C12Q 1/70* (2006.01)
*C12Q 1/6883* (2018.01)

(52) U.S. Cl.
CPC ........... *C12Q 1/701* (2013.01); *C12Q 1/6883* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | | |
|---|---|---|---|---|
| 6,110,457 A * | 8/2000 | Belshe | ........... | A61K 39/155 424/93.2 |
| 2002/0081567 A1* | 6/2002 | Henrickson | ........... | C12O 1/6816 435/5 |
| 2006/0003340 A1* | 1/2006 | Kostrikis | ........... | C12Q 1/70 435/5 |
| 2006/0008810 A1* | 1/2006 | Lee | ........... | C12Q 1/701 435/6.1 |
| 2006/0014140 A1* | 1/2006 | Boivin | ........... | C07K 14/005 435/5 |
| 2006/0177849 A1 | 8/2006 | Oh et al. | | |
| 2006/0257852 A1* | 11/2006 | Rappuoli | ........... | C07K 14/005 435/5 |
| 2007/0087336 A1* | 4/2007 | Sampath | ........... | C12Q 1/701 435/5 |
| 2007/0092871 A1* | 4/2007 | Lodes | ........... | C12O 1/689 435/5 |
| 2008/0003565 A1* | 1/2008 | Baptista | ........... | C12Q 1/70 435/5 |
| 2009/0081648 A1* | 3/2009 | Wangh | ........... | C12Q 1/701 435/6.16 |
| 2009/0124512 A1 | 5/2009 | Rowlen et al. | | |
| 2009/0275636 A1* | 11/2009 | Briese | ........... | C07K 14/005 514/44 A |
| 2009/0305229 A1* | 12/2009 | McBride | ........... | C12Q 1/701 435/5 |
| 2010/0273156 A1* | 10/2010 | Hellyer | ........... | C12O 1/701 435/6.14 |
| 2013/0273531 A1 | 10/2013 | Arieli et al. | | |
| 2014/0127216 A1* | 5/2014 | Balraj | ........... | C12N 15/86 424/139.1 |

FOREIGN PATENT DOCUMENTS

| | | | |
|---|---|---|---|
| CN | 101812532 A | * | 8/2010 |
| EP | 1837403 A2 | | 9/2007 |
| JP | 2006-180878 A | | 7/2006 |
| JP | 2009-523451 A | | 6/2009 |
| JP | 2009-538146 A | | 11/2009 |
| KR | 10-2006-0073457 A | | 6/2006 |
| KR | 10-2007-0050672 | | 5/2007 |
| KR | 10-2008-0111661 A | | 12/2008 |
| KR | 10-2010-0129888 A | | 12/2010 |
| WO | WO 2007/057062 A1 | | 5/2007 |
| WO | WO 2009/009900 A1 | | 1/2009 |

OTHER PUBLICATIONS

Lieberman et al. (Identification of Respiratory Viruses in Adults: Nasopharyngeal versus Oropharyngeal Sampling, J. Clin. Microbiol. Nov. 2009 vol. 47 No. 11).*
Stratagene (Gene Characterization Kits; 1988).*
Weiner et al. (Kits and their unique role in molecular biology: a brief retrospective, BioTechniques 44:701-704 (25th Anniversary Issue, Apr. 2008)).*
Côté, S., et al., "Comparative Evaluation of Real-Time PCR Assays for Detection of Human Metapneumovirus," *Journal of Clinical Microbiology* 41(8):3631-3635, American Society for Microbiology, United States (2003).

(Continued)

*Primary Examiner* — Aaron A Priest
(74) *Attorney, Agent, or Firm* — Sterne, Kessler, Goldstein & Fox P.L.L.C.

(57) ABSTRACT

The present invention relates to a kit for simultaneous diagnosis of viral respiratory diseases. To be more specific, the present invention is directed to a method for diagnosing viral respiratory diseases by detecting the genes specific to the respiratory disease-causing virus, a primer set for diagnosing the viral respiratory diseases used in the diagnosis method, a composition for simultaneous diagnosis of viral respiratory diseases, comprising the primer set, and a kit for simultaneous diagnosis of viral respiratory diseases, comprising the composition. When the primer set of the present invention for diagnosing the viral respiratory diseases is used, 14 different types of respiratory viruses can be simultaneously detected only with one reaction through real-time multiplex reverse transcription (RT)-PCR, and the onset of respiratory diseases caused by these viruses can be diagnosed. Thus, the primer set of the present invention can be widely used for prompt diagnosis and treatment of respiratory diseases.

13 Claims, No Drawings
Specification includes a Sequence Listing.

(56) References Cited

OTHER PUBLICATIONS

Kuiken, T., et al., "Newly discovered coronavirus as the primary cause of severe acute respiratory syndrome," *The Lancet* 362:263-270, Lancet Publishing Group, England (2003).

International Search Report based on PCT/KR2012/001262 dated Sep. 28, 2012.

Emery, S.L., et al., "Real-Time Reverse Transcription—Polymerase Chain Reaction Assay for SARS-associated Coronavirus," *Emerging Infectious Disease* 10(2): 311-316, Centers for Disease Control and Prevention, United States (2004).

Templeton, K.E., et al., "Rapid and Senstive Method Using Multiplex Real-Time PCR for Diagnosis of Infections by Influenza A and Influenza B Viruses, Respiratory Syncytial Virus, and Parainfluenza Viruses 1, 2, 3, and 4," *Journal of Clinical Microbiology* 42(4): 1564-1569, American Society for Microbiology, United States (2004).

Alvarez-Buylla, A. et al., "Presence of Several Respiratory Viruses in Samples From Patients With Suspected Flu A/H1N1 Infection" Clin. Microbiology and Infection 16(supp. 2): S301, Decker Europe, England (2010).

Dina, J. et al., "Detection of human bocavirus in hospitalised children," Journal of Paediatrics and Child Health 45(3): 149-153, Paediatrics and Child Health Division (Royal Australasian College of Physicians), Australia (2009).

Jansen, R. R., et al.,"Development and Evaluation of a Four-Tube Real Time Multiplex PCR Assay Covering Fourteen Respiratory Viruses, and Comparison to Its Corresponding Single Target Counterparts," Journal of Clinical Virology 51(3):179-85, Elsevier Science, The Netherlands (2011).

Kapoor, A. , et al., "Human Bocaviruses Are Highly Diverse, Dispersed, Recombination Prone, and Prevalent Enteric Infections," The Journal of Infectious Diseases 201(11) : 1633-1643, Infectious Diseases Society of America, United States (2010).

Lee, B. E., et al., "Enhanced Identification of Viral and Atypical Bacterial Pathogens in Lower Respiratory Tract Samples With Nucleic Acid Amplification Tests," Journal of Medical Virology 78(5): 702-710, Wiley-Liss, United States (2006).

Lu, X., et al., "Real-Time PCR Assays for Detection of Bocavirus in Human Specimens," Journal of Clinical Microbiology 44(9): 3231-3235, American Society for Microbiolgy, United States (2006).

Mahony, J., el al., "Development of a Respiratory Virus Panel Test for Detection of Twenty Human Respiratory Viruses by Use of Multiplex PCR and a Fluid Microbead-Based Assay," Journal of Clinical Microbiology 45(9): 2965-2970, American Society for Microbiolgy, United States (2007).

Sizun, J. et al., "Comparison of Immunofluorescence With Monoclonal Antibodies and RT-PCR for 'The Detection of Human Coronaviruses 229E and OC43 in Cell Culture," Journal of Virological Methods 72(2):145-152, Elsevier, Netherlands (1998).

Smuts H. and Hardie D., "Human Bocavirus in Hospitalized Children, South Africa," Emerging Infectious Diseases, 12(9): 1457-1458, Centers for Disease Control and Prevention, United States (2006).

Suzuki, A., "Detection of Human Metapneumovirus From Wheezing Children in Japan," The Journal of the Japanese Association for Infectious Diseases. vol. 77, No. 6, pp. 467-468, Tokyo: Japanese Association for Infectious Diseases, Japan (2003).

Wisdom, A., et al., "Screening Respiratory Samples for Detection of Human Rhinoviruses (HRVs) and Enteroviruses: Comprehensive VP4-VP2 Typing Reveals High Incidence and Genetic Diversity of HRV Species C," Journal of Clinical Microbiology 47(12) : 3958-3967, American Society for Microbiology, United States (2009).

Extended European Search Report for EP Application No. EP 12 74 7732, Munich, Germany, dated May 5, 2015.

GenBank, "Human parainfluenza virus type 1 hemagglutinin/neuraminidase mRNA, complete cds," Accession No. M91648 M30696, accessed at https://www.ncbi.nlm.nih.gov/nucleotide/M91648?report=genbank&log$=nuclalign&blast_rank=3&RID=4TMZZ86M014#, Feb. 26, 2018.

GenBank, "Human parainfluenza virus 2 strain Riyadh 105/2009 hemagglutinin-neuramindase (HN) gene, complete cds," Accession No. HM460888, accessed at https://www.ncbi.nlm.nih.gov/nuccore/309252630?sat=17&satkey=23870620#, Feb. 26, 2018.

GenBank, "Human parainfluenza virus 3 strain Riyadh 149/2009 hemagglutinin-neuramindase (HN) gene, complete cds," Accession No. HM460887, accessed at https://www.ncbi.nlm.nih.gov/nuccore/309252628?sat=15&satkey=11135868#goto309252628_0, Feb. 26, 2018.

GenBank, "*Homo sapiens* mRNA for ribonuclease P variant, clone: KAT10347," Accession No. AK225532, accessed at https://www.ncbi.nlm.nih.gov/nucleotide/AK225532.1?report=genbank&log$=nucltop&blast_rank=41&RID=4VT233M4015#goto110623967_0, Feb. 26, 2018.

GenBank, "Human coronavirus OC43,complete genome," Accession No. AY391777.1, accessed at https://www.ncbi.nlm.nih.gov/nuccore/AY391777.1, Oct. 4, 2017.

\* cited by examiner

SEQUENCE LISTING

<160> NUMBER OF SEQ ID NOS: 52

<210> SEQ ID NO 1
<211> LENGTH: 20
<212> TYPE: DNA
<213> ORGANISM: Artificial Sequence
<220> FEATURE:
<223> OTHER INFORMATION: primer 229E-F

<400> SEQUENCE: 1
cagtcaaatg ggctgatgca                                               20

<210> SEQ ID NO 2
<211> LENGTH: 29
<212> TYPE: DNA
<213> ORGANISM: Artificial Sequence
<220> FEATURE:
<223> OTHER INFORMATION: primer 229E-R

<400> SEQUENCE: 2
aaagggctat aaagagaata aggtattct                                     29

<210> SEQ ID NO 3
<211> LENGTH: 21
<212> TYPE: DNA
<213> ORGANISM: Artificial Sequence
<220> FEATURE:
<223> OTHER INFORMATION: primer OC43-F

<400> SEQUENCE: 3
aygaggctat tccgactagg t                                             21

<210> SEQ ID NO 4
<211> LENGTH: 26
<212> TYPE: DNA
<213> ORGANISM: Artificial Sequence
<220> FEATURE:
<223> OTHER INFORMATION: primer OC43-R

<400> SEQUENCE: 4
cttcctgagc cttcaatata gtaacc                                        26

<210> SEQ ID NO 5
<211> LENGTH: 30
<212> TYPE: DNA
<213> ORGANISM: Artificial Sequence
<220> FEATURE:
<223> OTHER INFORMATION: primer NL63-F

<400> SEQUENCE: 5
acgtacttct attatgaagc atgatattaa                                    30

<210> SEQ ID NO 6
<211> LENGTH: 30
<212> TYPE: DNA
<213> ORGANISM: Artificial Sequence
<220> FEATURE:
<223> OTHER INFORMATION: primer NL63-R

<400> SEQUENCE: 6
agcagattta atgttatact taaaactacg                                    30

<210> SEQ ID NO 7
<211> LENGTH: 31
<212> TYPE: DNA
<213> ORGANISM: Artificial Sequence

```
<220> FEATURE:
<223> OTHER INFORMATION: primer PIV1-F

<400> SEQUENCE: 7
gttgtcaatg tcttaatycg tatcaataat t                              31

<210> SEQ ID NO 8
<211> LENGTH: 21
<212> TYPE: DNA
<213> ORGANISM: Artificial Sequence
<220> FEATURE:
<223> OTHER INFORMATION: primer PIV1-R

<400> SEQUENCE: 8
tagcctmccy tcggcaccta a                                         21

<210> SEQ ID NO 9
<211> LENGTH: 23
<212> TYPE: DNA
<213> ORGANISM: Artificial Sequence
<220> FEATURE:
<223> OTHER INFORMATION: primer PIV2-F

<400> SEQUENCE: 9
tttccaatyt tcaggactat gaa                                       23

<210> SEQ ID NO 10
<211> LENGTH: 22
<212> TYPE: DNA
<213> ORGANISM: Artificial Sequence
<220> FEATURE:
<223> OTHER INFORMATION: primer PIV2-R

<400> SEQUENCE: 10
tcctggtatr gcagtgactg aa                                        22

<210> SEQ ID NO 11
<211> LENGTH: 26
<212> TYPE: DNA
<213> ORGANISM: Artificial Sequence
<220> FEATURE:
<223> OTHER INFORMATION: primer PIV3-2-F

<400> SEQUENCE: 11
caggatatag gaaaatcata tcaagt                                    26

<210> SEQ ID NO 12
<211> LENGTH: 27
<212> TYPE: DNA
<213> ORGANISM: Artificial Sequence
<220> FEATURE:
<223> OTHER INFORMATION: primer PIV3-2-R

<400> SEQUENCE: 12
acatgactty ctattgtcat ttatgtt                                   27

<210> SEQ ID NO 13
<211> LENGTH: 20
<212> TYPE: DNA
<213> ORGANISM: Artificial Sequence
<220> FEATURE:
<223> OTHER INFORMATION: primer IfA-F

<400> SEQUENCE: 13
agaccaatyy tgtcacctct                                           20
```

<210> SEQ ID NO 14
<211> LENGTH: 19
<212> TYPE: DNA
<213> ORGANISM: Artificial Sequence
<220> FEATURE:
<223> OTHER INFORMATION: primer IfA-R

<400> SEQUENCE: 14
tggacaaakc gtctacgct                                            19

<210> SEQ ID NO 15
<211> LENGTH: 19
<212> TYPE: DNA
<213> ORGANISM: Artificial Sequence
<220> FEATURE:
<223> OTHER INFORMATION: primer RNaseP-F

<400> SEQUENCE: 15
agatttggac ctgcgagcg                                            19

<210> SEQ ID NO 16
<211> LENGTH: 20
<212> TYPE: DNA
<213> ORGANISM: Artificial Sequence
<220> FEATURE:
<223> OTHER INFORMATION: primer RNaseP-R

<400> SEQUENCE: 16
gagcggctgt ctccacaagt                                           20

<210> SEQ ID NO 17
<211> LENGTH: 26
<212> TYPE: DNA
<213> ORGANISM: Artificial Sequence
<220> FEATURE:
<223> OTHER INFORMATION: primer IfB-F

<400> SEQUENCE: 17
aartacggtg gattaaayaa aagcaa                                    26

<210> SEQ ID NO 18
<211> LENGTH: 28
<212> TYPE: DNA
<213> ORGANISM: Artificial Sequence
<220> FEATURE:
<223> OTHER INFORMATION: primer IfB-R

<400> SEQUENCE: 18
aatagttttg caggmggtct atatttgg                                  28

<210> SEQ ID NO 19
<211> LENGTH: 25
<212> TYPE: DNA
<213> ORGANISM: Artificial Sequence
<220> FEATURE:
<223> OTHER INFORMATION: primer RSV A-1-F

<400> SEQUENCE: 19
attgttatca ttaattgctg ttgga                                     25

<210> SEQ ID NO 20
<211> LENGTH: 29
<212> TYPE: DNA
<213> ORGANISM: Artificial Sequence
<220> FEATURE:
<223> OTHER INFORMATION: primer RSV A-1-R

<400> SEQUENCE: 20
ctaaatgcaa tattatttat accactcag                                              29

<210> SEQ ID NO 21
<211> LENGTH: 25
<212> TYPE: DNA
<213> ORGANISM: Artificial Sequence
<220> FEATURE:
<223> OTHER INFORMATION: primer RSV B-1-F

<400> SEQUENCE: 21
tgcagtraca gaattacagc tactt                                                  25

<210> SEQ ID NO 22
<211> LENGTH: 25
<212> TYPE: DNA
<213> ORGANISM: Artificial Sequence
<220> FEATURE:
<223> OTHER INFORMATION: primer RSV B-1-R

<400> SEQUENCE: 22
ttagtggtat tgattgtrta gttca                                                  25

<210> SEQ ID NO 23
<211> LENGTH: 20
<212> TYPE: DNA
<213> ORGANISM: Artificial Sequence
<220> FEATURE:
<223> OTHER INFORMATION: primer MPV-2-F

<400> SEQUENCE: 23
tcatcaggya ayatyccaca                                                        20

<210> SEQ ID NO 24
<211> LENGTH: 23
<212> TYPE: DNA
<213> ORGANISM: Artificial Sequence
<220> FEATURE:
<223> OTHER INFORMATION: primer MPV-2-R

<400> SEQUENCE: 24
acttctatdg ttgatgctag ytt                                                    23

<210> SEQ ID NO 25
<211> LENGTH: 21
<212> TYPE: DNA
<213> ORGANISM: Artificial Sequence
<220> FEATURE:
<223> OTHER INFORMATION: primer AdV-F
<220> FEATURE:
<221> NAME/KEY: misc_feature
<222> LOCATION: (4)..(4)
<223> OTHER INFORMATION: n is a, c, g or t

<400> SEQUENCE: 25
cacngtgggg tttctraact t                                                      21

<210> SEQ ID NO 26
<211> LENGTH: 21
<212> TYPE: DNA
<213> ORGANISM: Artificial Sequence
<220> FEATURE:
<223> OTHER INFORMATION: primer AdV-R

<400> SEQUENCE: 26
cartggkcwt acatgcayat c                                                      21

<210> SEQ ID NO 27
<211> LENGTH: 18
<212> TYPE: DNA
<213> ORGANISM: Artificial Sequence
<220> FEATURE:
<223> OTHER INFORMATION: primer RV-1-F

<400> SEQUENCE: 27
tgtgaagagc cscrtgtg                                             18

<210> SEQ ID NO 28
<211> LENGTH: 20
<212> TYPE: DNA
<213> ORGANISM: Artificial Sequence
<220> FEATURE:
<223> OTHER INFORMATION: primer RV-2-F

<400> SEQUENCE: 28
tgtgaagact cgcatgtgct                                           20

<210> SEQ ID NO 29
<211> LENGTH: 21
<212> TYPE: DNA
<213> ORGANISM: Artificial Sequence
<220> FEATURE:
<223> OTHER INFORMATION: primer RV-3-F
<220> FEATURE:
<221> NAME/KEY: misc_feature
<222> LOCATION: (15)..(15)
<223> OTHER INFORMATION: n is a, c, g, or t

<400> SEQUENCE: 29
gtgygaagag yctantgtgc t                                         21

<210> SEQ ID NO 30
<211> LENGTH: 22
<212> TYPE: DNA
<213> ORGANISM: Artificial Sequence
<220> FEATURE:
<223> OTHER INFORMATION: primer RV-R

<400> SEQUENCE: 30
ggacrcccaa agtagtyggt yc                                        22

<210> SEQ ID NO 31
<211> LENGTH: 22
<212> TYPE: DNA
<213> ORGANISM: Artificial Sequence
<220> FEATURE:
<223> OTHER INFORMATION: primer RV-2-R

<400> SEQUENCE: 31
ggacayccaa agtagtyggt yc                                        22

<210> SEQ ID NO 32
<211> LENGTH: 23
<212> TYPE: DNA
<213> ORGANISM: Artificial Sequence
<220> FEATURE:
<223> OTHER INFORMATION: primer BoV-1-F

<400> SEQUENCE: 32
gaaatgcttt ctgctgytga aag                                       23

<210> SEQ ID NO 33
<211> LENGTH: 23
<212> TYPE: DNA
<213> ORGANISM: Artificial Sequence
<220> FEATURE:
<223> OTHER INFORMATION: primer BoV-1-R

<400> SEQUENCE: 33
ggttcaccgt twtcaagwgg att                                              23

<210> SEQ ID NO 34
<211> LENGTH: 24
<212> TYPE: DNA
<213> ORGANISM: Artificial Sequence
<220> FEATURE:
<223> OTHER INFORMATION: probe 229E-P-rev

<400> SEQUENCE: 34
ccctgacgac cacgttgtgg ttca                                             24

<210> SEQ ID NO 35
<211> LENGTH: 21
<212> TYPE: DNA
<213> ORGANISM: Artificial Sequence
<220> FEATURE:
<223> OTHER INFORMATION: probe OC43-P

<400> SEQUENCE: 35
cgcctggcac ggtactccct c                                                21

<210> SEQ ID NO 36
<211> LENGTH: 30
<212> TYPE: DNA
<213> ORGANISM: Artificial Sequence
<220> FEATURE:
<223> OTHER INFORMATION: probe NL63-P

<400> SEQUENCE: 36
attgccaagg ctcctaaacg tacaggtgtt                                       30

<210> SEQ ID NO 37
<211> LENGTH: 32
<212> TYPE: DNA
<213> ORGANISM: Artificial Sequence
<220> FEATURE:
<223> OTHER INFORMATION: probe PIV1-P

<400> SEQUENCE: 37
aggccaaaga ttgttgtcga gacwattcca at                                    32

<210> SEQ ID NO 38
<211> LENGTH: 32
<212> TYPE: DNA
<213> ORGANISM: Artificial Sequence
<220> FEATURE:
<223> OTHER INFORMATION: probe PIV2-P

<400> SEQUENCE: 38
cyatttacct aagtgatgga atcaatcgca aa                                    32

<210> SEQ ID NO 39
<211> LENGTH: 30
<212> TYPE: DNA
<213> ORGANISM: Artificial Sequence
<220> FEATURE:
<223> OTHER INFORMATION: probe PIV3-2-P

```
<400> SEQUENCE: 39
cagacttggt acctgactta aatccyagga                                    30

<210> SEQ ID NO 40
<211> LENGTH: 18
<212> TYPE: DNA
<213> ORGANISM: Artificial Sequence
<220> FEATURE:
<223> OTHER INFORMATION: probe IfA-P

<400> SEQUENCE: 40
acgctcaccg tgcccagt                                                 18

<210> SEQ ID NO 41
<211> LENGTH: 23
<212> TYPE: DNA
<213> ORGANISM: Artificial Sequence
<220> FEATURE:
<223> OTHER INFORMATION: probe RNaseP-P

<400> SEQUENCE: 41
ttctgacctg aaggctctgc gcg                                           23

<210> SEQ ID NO 42
<211> LENGTH: 25
<212> TYPE: DNA
<213> ORGANISM: Artificial Sequence
<220> FEATURE:
<223> OTHER INFORMATION: probe IfB-P

<400> SEQUENCE: 42
tgcaaargcm ataggraatt gccca                                         25

<210> SEQ ID NO 43
<211> LENGTH: 29
<212> TYPE: DNA
<213> ORGANISM: Artificial Sequence
<220> FEATURE:
<223> OTHER INFORMATION: probe RSV A-1-P

<400> SEQUENCE: 43
ctgtaaggcc agaagcacac cartcacac                                     29

<210> SEQ ID NO 44
<211> LENGTH: 26
<212> TYPE: DNA
<213> ORGANISM: Artificial Sequence
<220> FEATURE:
<223> OTHER INFORMATION: probe RSV B-1-P

<400> SEQUENCE: 44
cgggccagaa gagaagcacc acagta                                        26

<210> SEQ ID NO 45
<211> LENGTH: 25
<212> TYPE: DNA
<213> ORGANISM: Artificial Sequence
<220> FEATURE:
<223> OTHER INFORMATION: probe MPV-2-P

<400> SEQUENCE: 45
cagagrccyt cagcaccaga cacac                                         25
```

```
<210> SEQ ID NO 46
<211> LENGTH: 25
<212> TYPE: DNA
<213> ORGANISM: Artificial Sequence
<220> FEATURE:
<223> OTHER INFORMATION: probe AdV-1-P

<400> SEQUENCE: 46
tgcaccagcc cggggctcag gtact                                      25

<210> SEQ ID NO 47
<211> LENGTH: 25
<212> TYPE: DNA
<213> ORGANISM: Artificial Sequence
<220> FEATURE:
<223> OTHER INFORMATION: probe AdV-2-P

<400> SEQUENCE: 47
tgcaccagac csggactcag gtact                                      25

<210> SEQ ID NO 48
<211> LENGTH: 25
<212> TYPE: DNA
<213> ORGANISM: Artificial Sequence
<220> FEATURE:
<223> OTHER INFORMATION: probe AdV-3-P

<400> SEQUENCE: 48
tgcaccaggc ccgggctcag rtact                                      25

<210> SEQ ID NO 49
<211> LENGTH: 25
<212> TYPE: DNA
<213> ORGANISM: Artificial Sequence
<220> FEATURE:
<223> OTHER INFORMATION: probe AdV-4-P

<400> SEQUENCE: 49
tgcaccagcc cggkactcag gtayt                                      25

<210> SEQ ID NO 50
<211> LENGTH: 23
<212> TYPE: DNA
<213> ORGANISM: Artificial Sequence
<220> FEATURE:
<223> OTHER INFORMATION: probe RV-P

<400> SEQUENCE: 50
ccggcccctg aatgyggcta ayc                                        23

<210> SEQ ID NO 51
<211> LENGTH: 23
<212> TYPE: DNA
<213> ORGANISM: Artificial Sequence
<220> FEATURE:
<223> OTHER INFORMATION: probe RV-2-P

<400> SEQUENCE: 51
ccggcyccyg aatgtggcta acc                                        23

<210> SEQ ID NO 52
<211> LENGTH: 21
<212> TYPE: DNA
<213> ORGANISM: Artificial Sequence
<220> FEATURE:
<223> OTHER INFORMATION: probe BoV-1-P
```

-continued

```
<400> SEQUENCE: 52
cctrgagggt gggtgctkcc t                                              21
```

US 10,106,860 B2

SIMULTANEOUS DIAGNOSIS KIT FOR A DISEASE DUE TO A RESPIRATORY VIRUS

REFERENCE TO SEQUENCE LISTING SUBMITTED ELECTRONICALLY

The content of the electronically submitted sequence listing (Name 2972.0030001_CorrectedSequenceListing_ascii; Size: 10KB bytes; and Date of Creation: Jan, 7, 2014) filed with the application is incorporated herein by reference in its entirety.

TECHNICAL FIELD

The present invention relates to a kit for simultaneous diagnosis of viral respiratory diseases. To be more specific, the present invention is directed to a method for diagnosing viral respiratory diseases by detecting the gene specific to the respiratory disease-causing virus, a primer set for diagnosing the viral respiratory diseases used in the diagnosis method, a composition for simultaneous diagnosis of viral respiratory diseases, comprising the primer set, and a kit for simultaneous diagnosis of viral respiratory diseases, comprising the composition.

BACKGROUND ART

A respiratory virus is the main cause of acute respiratory infection, which is regarded as the most common disease irrespective of age or gender. In particular, for infants, elders, or people with weak cardiopulmonary function and immunity, a respiratory infection may cause aftereffects, leading to death. Diseases associated with respiratory virus mostly start with cold symptoms and may cause other various symptoms such as pharyngitis, worsening of chronic asthma, and pneumonia. Early diagnosis of viral respiratory infection can prevent drug abuse of unnecessary antibiotics and identify a type of virus early, thereby allowing providing a suitable treatment to the patients.

Methods for detecting the respiratory virus include conventional culture, rapid cell culture, rapid antigen non-immunofluorescence tests, rapid antigen immunofluorescence based tests, and molecular methods that use electrophoresis. The cell culture, which is a standard test method, takes more than 5 to 9 days to get the test results, and thus it has limitations to be used for early diagnosis and treatment of viral respiratory infection. To resolve these limitations, a R-Mix viral culture, which gives the test results within 24 to 72 hours and has similar sensitivity to conventional culture, has been used, but this also has a limitation to be used for early diagnosis and treatment of the disease. Also, rapid antigen non-immunofluorescence test can give the test results fast, but has a disadvantage of yielding high false negative results, as it is less sensitive than the conventional culture. As for molecular methods that use electrophoresis, it has a good sensitivity, but has a risk of contamination since it is conducted in two steps, and also takes long time to perform.

With this background, in effort to develop a method for resolving the limitations of the detection method for respiratory virus, including low sensitivity, risk of contamination, and long performing time, the present inventors have developed the primer sets and probes that can amplify the genes that are specific to 14 types of viruses, and confirmed that when each of the primer set and probe is used, the 14 types of respiratory viruses can be diagnosed simultaneously with high sensitivity and specificity, thereby completing the present invention.

DISCLOSURE

Technical Problem

One object of the present invention is to provide a method for diagnosing viral respiratory diseases by detecting the genes specific to the respiratory disease-causing virus.

Another object of the present invention is to provide a primer set for diagnosing the viral respiratory diseases used in the diagnosis method.

Another object of the present invention is to provide a composition for simultaneous diagnosis of viral respiratory diseases, comprising the primer set.

Another object of the present invention is to provide a kit for simultaneous diagnosis of viral respiratory diseases, comprising the composition.

Technical Solution

As one embodiment to achieve the above objectives, the present invention provides a primer comprising a nucleotide sequence selected from the group consisting of SEQ ID Nos. 1 to 14 and 17 to 33 for determining the infection of respiratory virus.

As used herein, the term "diagnosis" refers to the determination of pathologic status. For the purpose of the present invention, diagnosis means determining the onset of diseases caused by respiratory viruses and the prognosis of the therapeutic treatment with antiviral agents, by confirming the expression of the genes specific to various existing respiratory viruses.

As used herein, the term "primer" refers to a nucleotide sequence having a short free 3' hydroxyl group, which can form a base pair with complementary template and function as a starting point for replicating template. A primer can initiate DNA synthesis in the presence of reagents for polymerization (e.g., DNA polymerase or reverse transcriptase) and four different deoxynucleoside triphospate (dNTP) in a suitable buffer and at an optimal temperature. According to the present invention, it is preferable that the primer consists of forward nucleotide sequence and reverse nucleotide sequence having 10 to 30 bases each.

The primer can amplify the gene specific to a respiratory virus through PCR for determining the infection of respiratory virus, and the respiratory virus includes, but is not particularly limited to, corona virus 229E, corona virus OC43, corona virus NL63, influenza A virus, influenza B virus, parainfluenza virus 1, parainfluenza virus 2, parainfluenza virus 3, respiratory syncytial virus A, respiratory syncytial virus B, adenovirus, rhino virus A, B, and C, metapneumovirus, and boca virus. The genes that can distinguish each of the respiratory virus from other viruses include, but is not particularly limited to, nucleoprotein (N) gene of corona virus 229E, nucleoprotein (N) gene of corona virus OC43, polyprotein (1a) gene of corona virus NL63, matrix protein (M) gene of influenza A virus, hemagglutinin (HA) gene of influenza B virus, hemagglutinin-neuraminidase (HN) gene of parainfluenza virus 1, hemagglutinin-neuraminidase (HN) gene of parainfluenza virus 2, hemagglutinin-neuraminidase (HN) gene of parainfluenza virus 3, fusion protein gene of respiratory syncytial virus A, fusion protein gene of respiratory syncytial virus B, hexon protein gene of adenovirus, 5'UTR of rhino virus A, B, and C, nucleoprotein (N) gene of metapneumovirus, and nucleocapsid protein (NP) gene and viral protein (VP) gene of boca virus.

The primers provided in the present invention are preferably, but not particularly limited to, a primer having a nucleotide sequence of SEQ ID No. 1 or 2 capable of amplifying nucleoprotein (N) gene of corona virus 229E; a primer having a nucleotide sequence of SEQ ID No. 3 or 4 capable of amplifying nucleoprotein (N) gene of corona virus OC43; a primer having a nucleotide sequence of SEQ ID No. 5 or 6 capable of amplifying polyprotein (1a) gene of corona virus NL63; a primer having a nucleotide sequence of SEQ ID No. 7 or 8 capable of amplifying hemagglutinin-neuraminidase (HN) gene of parainfluenza virus 1; a primer having a nucleotide sequence of SEQ ID No. 9 or 10 capable of amplifying hemagglutinin-neuraminidase (HN) gene of parainfluenza virus 2; a primer having a nucleotide sequence of SEQ ID No. 11 or 12 capable of amplifying hemagglutinin-neuraminidase (HN) gene of parainfluenza virus 3; a primer having a nucleotide sequence of SEQ ID No. 13 or 14 capable of amplifying matrix protein (M) gene of influenza A virus; a primer having a nucleotide sequence of SEQ ID No. 17 or 18 capable of amplifying hemagglutinin (HA) gene of influenza B virus; a primer having a nucleotide sequence of SEQ ID No. 19 or 20 capable of amplifying fusion protein gene of respiratory syncytial virus A; a primer having a nucleotide sequence of SEQ ID No. 21 or 22 capable of amplifying fusion protein gene of respiratory syncytial virus B; a primer having a nucleotide sequence of SEQ ID No. 25 or 26 capable of amplifying hexon protein gene of adenovirus; a primer having a nucleotide sequence of SEQ ID Nos. 27 to 31 capable of amplifying 5'UTR of rhino virus A, B, and C; a primer having a nucleotide sequence of SEQ ID No. 23 or 24 capable of amplifying nucleoprotein (N) gene of metapneumovirus; and a primer having a nucleotide sequence of SEQ ID No. 32 or 33 capable of amplifying nucleocapsid protein (NP) gene of boca virus. Also, the primer may comprise additional features as long as the basic function thereof acting as a starting point for DNA synthesis is not changed.

In addition, the nucleotide sequence of the primer of the present invention may comprise a marker, which is directly or indirectly detectable through spectroscopic method, photochemical method, biochemical method, immunochemical method, or chemical method, if necessary. Examples of the marker include enzyme (e.g., horseradish peroxidase and alkaline phosphatase), radioactive isotope (e.g., 32P), fluorescent molecule, and chemical groups (e.g., biotin).

Furthermore, the primer may be chemically synthesized by using phosphoramidite solid support or other methods widely known in the art. The nucleotide sequence of such primers can be modified by using various methods in the art, and preferably by methylation, capsulation, substitution of more than one native nucleotides by homologues, and addition of various linkers (e.g., methyl phosphonate, phosphotriester, phosphoramidite, carbamate, phosphorothioate, and phosphorodithioate), but is not limited thereto.

As another aspect to achieve the above objectives, the present invention provides a composition for simultaneous diagnosis of respiratory virus, comprising the primer set.

The composition for simultaneous diagnosis of respiratory virus of the present invention comprises a primer having a nucleotide sequence of SEQ ID No. 1 or 2 capable of amplifying nucleoprotein (N) gene of corona virus 229E; a primer having a nucleotide sequence of SEQ ID No. 3 or 4 capable of amplifying nucleoprotein (N) gene of corona virus OC43; a primer having a nucleotide sequence of SEQ ID No. 5 or 6 capable of amplifying polyprotein (1a) gene of corona virus NL63; a primer having a nucleotide sequence of SEQ ID Nos. 7 and 8 capable of amplifying hemagglutinin-neuraminidase (HN) gene of parainfluenza virus 1; a primer having a nucleotide sequence of SEQ ID Nos. 9 and 10 capable of amplifying hemagglutinin-neuraminidase (HN) gene of parainfluenza virus 2; a primer having a nucleotide sequence of SEQ ID Nos. 11 and 12 capable of amplifying hemagglutinin-neuraminidase (HN) gene of parainfluenza virus 3; a primer having a nucleotide sequence of SEQ ID Nos. 13 and 14 capable of amplifying matrix protein (M) gene of influenza A virus; a primer having a nucleotide sequence of SEQ ID Nos. 17 and 18 capable of amplifying hemagglutinin (HA) gene of influenza B virus; a primer having a nucleotide sequence of SEQ ID Nos. 19 and 20 capable of amplifying fusion protein gene of respiratory syncytial virus A; a primer having a nucleotide sequence of SEQ ID Nos. 21 and 22 capable of amplifying fusion protein gene of respiratory syncytial virus B; a primer having a nucleotide sequence of SEQ ID Nos. 25 and 26 capable of amplifying hexon protein gene of adenovirus; a primer having a nucleotide sequence of SEQ ID Nos. 27 to 31 capable of amplifying 5'UTR of rhino virus A, B, and C; a primer having a nucleotide sequence of SEQ ID Nos. 23 and 24 capable of amplifying nucleoprotein (N) gene of metapneumovirus; and a primer having a nucleotide sequence of SEQ ID Nos. 32 and 33 capable of amplifying nucleocapsid protein (NP) gene of boca virus. Preferably, the composition of the present invention comprises two or more primer sets consisting of the above-listed primer sets, and can be used for diagnosing two or more respiratory viruses simultaneously.

The composition may further comprise the probes having a nucleotide sequence selected from the group consisting of SEQ ID Nos. 34 to 40 and 42 to 52, for detecting respiratory virus-specific genes more efficiently.

As used herein, the term "probe" refers to a nucleotide fragment of RNA or DNA that is composed of several bases to several hundreds of bases, and that can bind specifically to a complementary nucleotide sequence. Since the probes are labeled, it can be used for detecting the presence of certain nucleotide sequences. Probes may be prepared in the form of oligonucleotide probe, single stranded DNA probe, double stranded DNA probe, and RNA probe. Also, for performing real-time PCR, a fluorescence-labeled probe may be used. More specifically, as for TaqMan probe, an oligonucleotide, whose 5' terminal is modified with fluorescent molecule and the 3' terminal is modified with quencher, is added to a PCR reaction. Also, the real-time PCR using cycling probe is a highly sensitive detection method, consisting of a chimeric probe composed of RNA, DNA and RNase H. For this method, 5' terminal of probe is labeled with fluorescent molecule and 3' terminal is labeled with quencher.

When real-time PCR is employed to detect the amplified product, the amplification of the product can be monitored in real time, and thus DNA and RNA can be quantified accurately, analyzed promptly and easily as electrophoresis is not required, and also there is low risk of contamination. Based on these facts, the present inventors have prepared a fluorescence-labeled probe for diagnosing respiratory virus more efficiently by employing real-time PCR. It is preferable to use a probe having a nucleotide sequence of SEQ ID No. 34 capable of detecting nucleoprotein (N) gene of corona virus 229E; a probe having a nucleotide sequence of SEQ ID No. 35 capable of detecting nucleoprotein (N) gene of corona virus OC43; a probe having a nucleotide sequence of SEQ ID No. 36 capable of detecting polyprotein (1a) gene of corona virus NL63; a probe having a nucleotide sequence of SEQ ID No. 37 capable of detecting hemagglutinin-neuraminidase (HN) gene of parainfluenza virus 1; a probe having a nucleotide sequence of SEQ ID No. 38 capable of detecting hemagglutinin-neuraminidase (HN) gene of parainfluenza virus 2; a probe having a nucleotide sequence of SEQ ID No. 39 capable of detecting hemagglutinin-neuraminidase (HN) gene of parainfluenza virus 3; a probe having a nucleotide sequence of SEQ ID No. 40 capable of detecting matrix protein (M) gene of influenza A virus; a probe having a nucleotide sequence of SEQ ID No. 42 capable of detecting hemagglutinin (HA) gene of influenza B virus; a probe having a nucleotide sequence of SEQ ID No. 43 capable of detecting fusion protein gene of respiratory syncytial virus A; a probe having a nucleotide sequence of SEQ ID No. 44 capable of detecting fusion protein gene of respiratory syncytial virus B; a probe having a nucleotide sequence of SEQ ID No. 45 capable of detecting nucleoprotein (N) gene of metapneumovirus; a probe having a nucleotide sequence of SEQ ID Nos. 46 to 49 capable of detecting hexon protein gene of adenovirus; a probe having a nucleotide sequence of SEQ ID Nos. 50 and 51 capable of detecting 5'UTR of rhino virus A, B, and C; and a probe having a nucleotide sequence of SEQ ID No. 52 capable of detecting nucleocapsid protein (NP) gene and viral protein (VP) gene of boca virus, but is not particularly limited thereto.

Also, in order to provide a standard for determining validity of RNA extraction, a primer having a nucleotide sequence of SEQ ID Nos. 15 and 16 as a human RNase P-targeting internal control primer or a probe having a nucleotide sequence of SEQ ID No. 41 may be further added to the composition.

Furthermore, as similar to the primers, the probes provided in the present invention may be chemically synthesized by using phosphoramidite solid support or other methods widely known in the art. The nucleotide sequence of such probes can be modified by using various methods in the art, and preferably by methylation, capsulation, substitution of more than one native nucleotides by homologues, and addition of various linkers (e.g., methyl phosphonate, phosphotriester, phosphoramidite, carbamate, phosphorothioate, and phosphorodithioate), but is not limited thereto.

The composition for diagnosing respiratory virus of the present invention may further comprise a DNA polymerase for performing PCR in addition to the probes, and the DNA polymerase is preferably a hot start Taq DNA polymerase, but is not particularly limited thereto.

Also, the composition for diagnosing respiratory virus of the present invention may use the RNA extracted from the sample as a target sample. To use RNA as a sample, reverse transcriptase (RT)-PCR needs to be performed additionally, and it also needs to be confirmed whether the respiratory virus-specific gene is present in the PCR product. Thus the composition may further comprise a reverse transcriptase for performing RT-PCR, in addition to the probes and DNA polymerase.

As another aspect to achieve the above objectives, the present invention provides a kit for simultaneous diagnosis of respiratory viruses, comprising the primer set or the composition.

The kit for simultaneous diagnosis of respiratory viruses of the present invention comprises two or more or the primer sets or the composition as similar to the above-described composition for diagnosing respiratory viruses, and thus can be used for simultaneous diagnosis of two or more of the respiratory viruses.

Also, the kit of the present invention may further comprise one or more types of compositions, solutions, or devices having different constituents that are suitable for the purposes of analysis. For instance, the kit for diagnosis of the present invention may be a kit for simultaneous diagnosis of respiratory viruses that further comprises a reverse transcriptase, which is a required constituent for performing RT-PCR and multiplex real-time PCR and for synthesizing a complementary DNA (cDNA) of RNA, i.e., respiratory virus gene, in addition to the primer set specific to a target gene; a DNA polymerase for amplifying cDNA; a tube or other suitable container; a reaction buffer (with various pH levels and magnesium concentration); deoxynucleotides (dNTPs); enzymes such as hot start Taq-polymerase and reverse transcriptase; DNase and RNase inhibitors; DEPC-water; and sterilized water, but is not limited thereto.

As another aspect to achieve the above objectives, the present invention provides a method for diagnosing viral respiratory diseases by using the composition or the kit, or a method for providing the information for diagnosing viral respiratory diseases.

To be more specific, the method for diagnosing viral respiratory diseases of the present invention comprises (i) preparing a reaction mixture by mixing the primer, the probe, a DNA polymerase and a reverse transcriptase; (ii) obtaining a reaction product by adding DNA or RNA from a sample to the reaction mixture and successively performing Reverse transcription-PCR and real-time PCR; and (iii) detecting 1 to 14 types of the disease-causing viruses simultaneously by analyzing the reaction product. The respiratory viruses preferably include, but are not limited to, corona virus 229E, corona virus OC43, corona virus NL63, influenza A virus, influenza B virus, parainfluenza virus 1, parainfluenza virus 2, parainfluenza virus 3, respiratory syncytial virus A, respiratory syncytial virus B, adenovirus, rhino virus A, B, and C, metapneumovirus, and boca virus.

As used herein, the term "sample" refers to the samples such as saliva and sputum (e.g., nasopharyngeal swabs (NPS), nasal swabs (NS), throat swabs (TS), and nasal aspirates (NA)), wherein the expression level of the genes specific to each of the viruses changes by the infection of various respiratory viruses, but is not limited thereto.

Advantageous Effects

When the primer set of the present invention for diagnosing the viral respiratory diseases is used, 14 different types of respiratory viruses can be simultaneously detected only with one reaction through real-time multiplex reverse transcription (RT)-PCR, and the onset of respiratory diseases caused by these viruses can be diagnosed. Thus, the primer set of the present invention can be widely used for prompt diagnosis and treatment of respiratory diseases.

MODE FOR INVENTION

Hereinafter, the present invention will be described in more detail with reference to Examples. However, these Examples are for illustrative purposes only, and the invention is not intended to be limited by these Examples.

EXAMPLE 1

Preparation of Respiratory Virus-specific Primers and Probes

The present inventors prepared the primers and probes for detecting and distinguishing 14 types of respiratory viruses in the aspirate of rhinopharynx or swab samples (e.g., nasopharyngeal swabs (NPS), nasal swabs (NS), throat swabs (TS), nasal aspirates (NA)).

EXAMPLE 1-1

Preparation of Respiratory Virus-specific Primers

The present inventors prepared a primer pair having a nucleotide sequence of SEQ ID Nos. 1 and 2 capable of amplifying nucleoprotein (N) gene of corona virus 229E; a primer pair having a nucleotide sequence of SEQ ID Nos. 3 and 4 capable of amplifying nucleoprotein (N) gene of corona virus OC43; a primer pair having a nucleotide sequence of SEQ ID Nos. 5 and 6 capable of amplifying polyprotein (1a) gene of corona virus NL63; a primer pair having a nucleotide sequence of SEQ ID Nos. 7 and 8 capable of amplifying hemagglutinin-neuraminidase (HN) gene of parainfluenza virus 1; a primer pair having a nucleotide sequence of SEQ ID Nos. 9 and 10 capable of amplifying hemagglutinin-neuraminidase (HN) gene of parainfluenza virus 2; a primer pair having a nucleotide sequence of SEQ ID Nos. 11 and 12 capable of amplifying hemagglutinin-neuraminidase (HN) gene of parainfluenza virus 3; a primer pair having a nucleotide sequence of SEQ ID Nos. 13 and 14 capable of amplifying matrix protein (M) gene of influenza A virus; a primer pair having a nucleotide sequence of SEQ ID Nos. 15 and 16, which provides a standard for determining validity of RNA extraction; a primer pair having a nucleotide sequence of SEQ ID Nos. 17 and 18 capable of amplifying hemagglutinin (HA) gene of influenza B virus; a primer pair having a nucleotide sequence of SEQ ID Nos. 19 and 20 capable of amplifying fusion protein gene of respiratory syncytial virus A; a primer pair having a nucleotide sequence of SEQ ID Nos. 21 and 22 capable of amplifying fusion protein gene of respiratory syncytial virus B; a primer pair having a nucleotide sequence of SEQ ID Nos. 25 and 26 capable of amplifying hexon protein gene of adenovirus; a primer pair having a nucleotide sequence of SEQ ID Nos. 27 to 31 capable of amplifying 5′UTR of rhino virus A, B, and C; a primer pair having a nucleotide sequence of SEQ ID Nos. 23 and 24 capable of amplifying nucleoprotein (N) gene of metapneumovirus; and a primer pair having a nucleotide sequence of SEQ ID Nos. 32 and 33 capable of amplifying nucleocapsid protein (NP) gene and viral protein (VP) gene of boca virus, by using conventional method (see Table 1).

TABLE 1

Nucleotide Sequence of Primers

| Name | Nucleotide Sequence | Length | SEQ ID NO. |
| --- | --- | --- | --- |
| 229E-F | CAGTCAAATGGGCTGATGCA | 20 | 1 |
| 229E-R | AAAGGGCTATAAAGAGAATAAGGTATTCT | 29 | 2 |
| OC43-F | AYGAGGCTATTCCGACTAGGT | 21 | 3 |
| OC43-R | CTTCCTGAGCCTTCAATATAGTAACC | 26 | 4 |
| NL63-F | ACGTACTTCTATTATGAAGCATGATATTAA | 30 | 5 |
| NL63-R | AGCAGATTTAATGTTATACTTAAAACTACG | 30 | 6 |
| PIV1-F | GTTGTCAATGTCTTAATYCGTATCAATAATT | 31 | 7 |

TABLE 1-continued

Nucleotide Sequence of Primers

| Name | Nucleotide Sequence | Length | SEQ ID NO. |
| --- | --- | --- | --- |
| PIV1-R | TAGCCTMCCYTCGGCACCTAA | 21 | 8 |
| PIV2-F | TTTCCAATYTTCAGGACTATGAA | 25 | 9 |
| PIV2-R | TCCTGGTATRGCAGTGACTGAA | 26 | 10 |
| PIV3-2-F | CAGGATATAGGAAAATCATATCAAGT | 26 | 11 |
| PIV3-2-R | ACATGACTTYCTATTGTCATTTATGTT | 27 | 12 |
| IfA-F | AGACCAATYYTGTCACCTCT | 20 | 13 |
| IfA-R | TGGACAAAKCGTCTACGCT | 19 | 14 |
| RNaseP-F | AGATTTGGACCTGCGAGCG | 19 | 15 |
| RNaseP-R | GAGCGGCTGTCTCCACAAGT | 20 | 16 |
| IfB-F | AARTACGGTGGATTAAAYAAAAGCAA | 26 | 17 |
| IfB-R | AATAGTTTTGCAGGMGGTCTATATTTGG | 28 | 18 |
| RSV A-1-F | ATTGTTATCATTAATTGCTGTTGGA | 25 | 19 |
| RSV A-1-R | CTAAATGCAATATTATTTATACCACTCAG | 29 | 20 |
| RSV B-1-F | TGCAGTRACAGAATTACAGCTACTT | 25 | 21 |
| RSV B-1-R | TTAGTGGTATTGATTGTRTAGTTCA | 25 | 22 |
| MPV-2-F | TCATCAGGYAAYATYCCACA | 20 | 23 |
| MPV-2-R | ACTTCTATDGTTGATGCTAGYTT | 23 | 24 |
| AdV-F | CACNGTGGGGTTTCTRAACTT | 21 | 25 |
| AdV-R | CARTGGKCWTACATGCAYATC | 21 | 26 |
| RV-1-F | TGTGAAGAGCCSCRTGTG | 18 | 27 |
| RV-2-F | TGTGAAGACTCGCATGTGCT | 20 | 28 |
| RV-3-F | GTGYGAAGAGYCTANTGTGCT | 21 | 29 |
| RV-R | GGACRCCCAAAGTAGTYGGTYC | 22 | 30 |
| RV-2-R | GGACAYCCAAAGTAGTYGGTYC | 22 | 31 |
| BoV-1-F | GAAATGCTTTCTGCTGYTGAAAG | 23 | 32 |
| BoV-1-R | GGTTCACCGTTWTCAAGWGGATT | 23 | 33 |

EXAMPLE 1-2

Preparation of Respiratory Virus-specific Probes

The present inventors prepared a probe having a nucleotide sequence of SEQ ID No. 34 capable of detecting nucleoprotein (N) gene of corona virus 229E; a probe having a nucleotide sequence of SEQ ID No. 35 capable of detecting nucleoprotein (N) gene of corona virus OC43; a probe having a nucleotide sequence of SEQ ID No. 36 capable of detecting polyprotein (1a) gene of corona virus NL63; a probe having a nucleotide sequence of SEQ ID No. 37 capable of detecting hemagglutinin-neuraminidase (HN) gene of parainfluenza virus 1; a probe having a nucleotide sequence of SEQ ID No. 38 capable of detecting hemagglutinin-neuraminidase (HN) gene of parainfluenza virus 2; a probe having a nucleotide sequence of SEQ ID No. 39 capable of detecting hemagglutinin-neuraminidase (HN)

gene of parainfluenza virus 3; a probe having a nucleotide sequence of SEQ ID No. 40 capable of detecting matrix protein (M) gene of influenza A virus; a probe having a nucleotide sequence of SEQ ID No. 41 capable of detecting RNase P, as internal control; a probe having a nucleotide sequence of SEQ ID No. 42 capable of detecting hemagglutinin (HA) gene of influenza B virus; a probe having a nucleotide sequence of SEQ ID No. 43 capable of detecting fusion protein gene of respiratory syncytial virus A; a probe having a nucleotide sequence of SEQ ID No. 44 capable of detecting fusion protein gene of respiratory syncytial virus B; a probe having a nucleotide sequence of SEQ ID No. 45 capable of detecting nucleoprotein (N) gene of metapneumovirus; a probe having a nucleotide sequence of SEQ ID Nos. 46 to 49 capable of detecting hexon protein gene of adenovirus; a probe having a nucleotide sequence of SEQ ID Nos. 50 and 51 capable of detecting 5'UTR of rhino virus A, B, and C; and a probe having a nucleotide sequence of SEQ ID No. 52 capable of detecting nucleocapsid protein (NP) gene of boca virus, by using a conventional method (see Table 2).

TABLE 2

Nucleotide Sequences of Probes

| Name | 5' Nucleotide Sequence 3' | Length | SEQ ID No. |
|---|---|---|---|
| 229E-P-rev | FAM CCCTGACGACCACGTTGTGGTTCA TAMRA | 24 | 34 |
| OC43-P | HEX CGCCTGGCACGGTACTCCCTC TAMRA | 21 | 35 |
| NL63-P | Cy5 ATTGCCAAGGCTCCTAAACGTACAGBHQ3 GTGTT | 30 | 36 |
| PIV1-P | FAM AGGCCAAAGATTGTTGTCGAGACWATAMRA TTCCAAT | 32 | 37 |
| PIV2-P | HEX CYATTTACCTAAGTGATGGAATCAATAMRA TCGCAAA | 31 | 38 |
| PIV3-2-P | Cy5 CAGACTTGGTACCTGACTTAAATCCBHQ3 YAGGA | 30 | 39 |
| IfA-P | FAM ACGCTCACCGTGCCCAGT TAMRA | 18 | 40 |
| RNaseP-P | HEX TTCTGACCTGAAGGCTCTGCGCG TAMRA | 23 | 41 |
| IfB-P | Cy5 TGCAAARGCMATAGGRAATTGCCCABHQ3 | 25 | 42 |
| RSV A-1-P | FAM CTGTAAGGCCAGAAGCACACCARTCTAMRA ACAC | 29 | 43 |
| RSV B-1-P | Cy5 CGGGCCAGAAGAGAAGCACCACAGTBHQ3 A | 26 | 44 |
| MPV-2-P | HEX CAGAGRCCYTCAGCACCAGACACACTAMRA | 25 | 45 |
| AdV-1-P | FAM TGCACCAGCCCGGGGCTCAGGTACTTAMRA | 25 | 46 |
| AdV-2-P | FAM TGCACCAGACCSGGACTCAGGTACTTAMRA | 25 | 47 |
| AdV-3-P | FAM TGCACCAGGCCCGGGCTCAGRTACTTAMRA | 25 | 48 |
| AdV-4-P | FAM TGCACCAGCCCGGKACTCAGGTAYTTAMRA | 25 | 49 |
| RV-P | HEX CCGGCCCCTGAATGYGGCTAAYC TAMRA | 23 | 50 |
| RV-2-P | HEX CCGGCYCCYGAATGTGGCTAACC TAMRA | 23 | 51 |
| BoV-1-P | Cy5 CCTRGAGGGTGGGTGCTKCCT BHQ3 | 21 | 52 |

EXAMPLE 2

Diagnosis of Respiratory Viruses

EXAMPLE 2-1

Preparation of Required Reagents

The reagents shown in Table 3 were prepared. These reagents were thawed at a room temperature immediately prior to use, and preferably should not be left at a room temperature for more than 30 minutes.

TABLE 3

Composition and Constituents of Reagents

| No. | Composition | Constituents | SEQ ID No. |
|---|---|---|---|
| 1 | RT-PCR Premix | One-step RT-PCR premix | |
| 2 | Primer/Probe Mixture 1 | Corona Virus primer/probe mix | |
| | | 1. 229E primer probe mix (FAM) | 1-2, 34 |
| | | 2. OC43 primer probe mix (HEX) | 3-4, 35 |
| | | 3. NL63 primer probe mix (Cy5) | 5-6, 36 |
| 3 | Primer/Probe Mixture 2 | Parainfluenza Virus (PIV)primer/probe mix | |
| | | 1. PIV1 primer/probe mix (FAM) | 7-8, 37 |
| | | 2. PIV2 primer/probe mix (HEX) | 9-10, 38 |
| | | 3. PIV3 primer/probe mix (Cy5) | 11-12, 39 |
| 4 | Primer/Probe Mixture 3 | Influenza Virus/RNase P primer/probe mix | |
| | | 1. Influenza A primer/probe mix (FAM) | 13-14, 40 |
| | | 2. RNase P primer/probe mix (HEX) | 15-16, 41 |
| | | 3. Influenza B primer/probe mix (Cy5) | 17-18, 42 |
| 5 | Primer/Probe Mixture 4 | Respiratory syncytial Virus (RSV) primer/probe mix | |
| | | 1. RSV A primer/probe mix (FAM) | 19-20, 43 |
| | | 2. RSV B primer/probe mix (Cy5) | 21-22, 44 |
| | | 3. Metapneumovirus primer/probe mix (HEX) | 23-24, 45 |
| 6 | Primer/Probe Mixture 5 | Adenovirus/Rhino Virus primer probe mix | |
| | | 1. Adenovirus primer/probe mix (FAM) | 25-26, 46-49 |
| | | 2. Rhino Virus A, B, C primer/probe mix (HEX) | 27-31, 50-51 |
| | | 3. Boca Virus primer/probe mix (Cy5) | 32-33, 52 |
| 7 | Positive Control | Positive control containing 12 types of Respiratory Virus, RNase P primer/probe binding sequences | |
| 8 | Negative Control | Negative control containing RNase P primer/probe binding sequences | |

EXAMPLE 2-2

Preparation of Samples

For the experiments, aspirate of rhinopharynx or swab samples were used as a sample to analyze (e.g., nasopharyngeal swabs (NPS), nasal swabs (NS), throat swabs (TS), and nasal aspirates (NA)).

EXAMPLE 2-3

Method for Diagnosing Respiratory Viruses

The RNA sample was extracted from the sample prepared in Example 2-2 by using a RNA extraction kit. The 2000 μl PCR tubes had 100 μl of RT-PCR Premix added and were prepared in an amount equal to the sum of the number of samples, the positive control, and the negative control. The 5 μl of RVP primer/probe mixture and 5 μl of extracted sample, positive control, or negative control were added to each of the prepared RT-PCR Premix tubes (see Table 4).

TABLE 4

Samples and Compositions

| Name of sample and composition | | Used Amount per 1 test (μl) |
|---|---|---|
| | RT-PCR Premix | 10 |
| | RV primer/probe mixture | 5 |
| Amount of sample injected | Extracted sample, positive control, or negative control | 5 |
| | Total | 20 |

The tubes were sealed with a cap, centrifuged, and mixed well. After centrifuging, the samples were put in a real-time PCR cycler and the reaction started. The detailed conditions for real-time PCR are shown below (see Table 5).

TABLE 5

Conditions for real-time PCR

| | Steps | Temperature | Duration | Repeated times |
|---|---|---|---|---|
| Reverse-transcription | Step 1 | 45° C. | 10 minutes | 1 time |
| PCR | Step 2 | 94° C. | 5 minutes | |
| | Step 3 | 94° C. | 5 seconds | 40 times (*signal detection) |
| | Step 4 | 53° C. | 30 seconds | |
| | Step 5* | 72° C. | 30 seconds | |

Results of PCR analysis were measured in real time by a real-time PCR detection system, and once the reaction was finished, the cut-off value was entered (name of equipments: SLAM, FAM: 0.06, HEX: 0.06, CY5: 0.04).

EXAMPLE 2-4

Analysis of Results (1) Threshold cycle (CT) value of control groups

When the control groups were analyzed by PCR, the threshold cycle (CT) values thereof (i.e., the number of cycles over threshold value) were as follows (see Tables 6 and 7). Based on this, when the CT value of a sample was below 37 under each category (FAM, HEX, and CY5), the sample was determined as positive (see Tables 6 and 7)

TABLE 6

Standards for positive control

| Positive control | FAM | HEX | CY5 |
|---|---|---|---|
| primer/probe mixture 1 | 30 ± 3 | 30 ± 3 | 30 ± 3 |
| primer/probe mixture 2 | 30 ± 3 | 30 ± 3 | 30 ± 3 |
| primer/probe mixture 3 | 30 ± 3 | 30 ± 3 | 30 ± 3 |
| primer/probe mixture 4 | 30 ± 3 | 30 ± 3 | 30 ± 3 |
| primer/probe mixture 5 | 30 ± 3 | 30 ± 3 | 30 ± 3 |

TABLE 7

Standards for negative control

| Negative control | FAM | HEX | CY5 |
|---|---|---|---|
| primer/probe mixture 1 | No Ct | No Ct | No Ct |
| primer/probe mixture 2 | No Ct | No Ct | No Ct |
| primer/probe mixture 3 | No Ct | 30 ± 3 | No Ct |
| primer/probe mixture 4 | No Ct | No Ct | No Ct |
| primer/probe mixture 5 | No Ct | No Ct | No Ct |

As shown in Tables 6 and 7, the results could be validated only when the positive controls have a CT value within a range of 30±3 for each wavelength, and the negative controls show a CT value only for RNase P, which is an internal control, but not for the rest of respiratory viruses.

(2) Analysis of Results

For each reaction, a signal formation from FAM, HEX, and CY5 wavelength was confirmed, and the reaction validity, and positivity and negativity of viral respiratory infection were examined as shown below (see Table 8).

TABLE 8

Standards for determining a reaction validity and positivity and negativity of infection

| Category | FAM | HEX | CY5 | Result analysis |
|---|---|---|---|---|
| Primer/probe Mixture 1 | + | − | − | 229E |
| | − | + | − | OC43 |
| | − | − | + | NL63 |
| | − | − | − | Corona Virus negative |
| Primer/probe Mixture 2 | + | − | − | PIV1 |
| | − | + | − | PIV2 |
| | − | − | + | PIV3 |
| | − | − | − | Parainfluenza Virus negative |
| Primer/probe Mixture 3 | + | + | − | Influenza A |
| | − | + | + | Influenza B |
| | − | + | − | Influenza A/B negative |
| | − | − | − | Re-test |
| Primer/probe Mixture 4 | + | − | − | RSV A |
| | − | − | + | RSV B |
| | − | − | + | Metapneumovirus |
| | − | − | − | RSV A/B/Metapneumovirus negative |
| Primer/probe Mixture 5 | + | − | − | Adenovirus |
| | − | + | − | Rhino Virus A, B, C |
| | − | − | + | Boca Virus |
| | − | − | − | Adeno/Rhino/Boca Virus negative |

Table 8 shows the analysis result of the samples under each category, demonstrating the positivity and negativity of respiratory viruses. For instance, if CT value is below 37 for FAM only (positive) when primer/probe mixture 1 is used, this indicates that the subject is infected by corona virus 229E. Also, in Table 8, "Re-test" means that an internal control could not be detected, and thus the sample has to be re-tested.

The invention claimed is:

1. A method for diagnosing viral respiratory diseases, comprising
   (i) amplifying DNA or RNA in a sample isolated from a subject who has developed or is suspected of having the viral respiratory disease by using a primer set consisting of a primer pair consisting of SEQ ID Nos.: 1 and 2; a primer pair consisting of SEQ ID Nos. 3 and 4; a primer pair consisting of SEQ ID Nos. 5 and 6; a primer pair consisting of SEQ ID Nos. 7 and 8; a primer pair consisting of SEQ ID Nos. 9 and 10; a primer pair consisting of SEQ ID Nos. 11 and 12; a primer pair consisting of SEQ ID Nos. 13 and 14; a primer pair consisting of SEQ ID Nos. 17 and 18; a primer pair consisting of SEQ ID Nos. 19 and 20; a primer pair consisting of SEQ ID Nos. 21 and 22; a primer pair consisting of SEQ ID Nos. 23 and 24; a primer pair consisting of SEQ ID Nos. 25 and 26; a primer pair composed of a forward primer having a nucleotide sequence selected from the group consisting of SEQ ID Nos. 27 to 29 and a reverse primer having a nucleotide sequence selected from the group consisting of SEQ ID Nos. 30 and 31; and a primer pair consisting of SEQ ID Nos. 32 and 33; and
   (ii) simultaneously detecting two or more types of viruses selected from the group consisting of corona virus 229E, corona virus OC43, corona virus NL63, parainfluenza virus 1, parainfluenza virus 2, parainfluenza virus 3, influenza A virus, influenza B virus, respiratory syncytial virus A, respiratory syncytial virus B, boca virus, adenovirus, rhino virus A, rhino virus B, rhino virus C, and metapneumovirus.

2. The method according to claim 1, wherein the sample is saliva or sputum.

3. A composition for simultaneous diagnosis of viral respiratory diseases, comprising: a primer pair consisting of SEQ ID Nos. 1 and 2; a primer pair consisting of SEQ ID Nos. 3 and 4; a primer pair consisting of SEQ ID Nos. 5 and 6; a primer pair consisting of SEQ ID Nos. 7 and 8; a primer pair consisting of SEQ ID Nos. 9 and 10; a primer pair consisting of SEQ ID Nos. 11 and 12; a primer pair consisting of SEQ ID Nos. 13 and 14; a primer pair consisting of SEQ ID Nos. 17 and 18; a primer pair consisting of SEQ ID Nos. 19 and 20; a primer pair consisting of SEQ ID Nos. 21 and 22; a primer pair consisting of SEQ ID Nos. 23 and 24; a primer pair consisting of SEQ ID Nos. 25 and 26; a primer pair composed of a forward primer having a nucleotide sequence selected from the group consisting of SEQ ID Nos. 27 to 29 and a reverse primer having a nucleotide sequence selected from the group consisting of SEQ ID Nos. 30 and 31; and a primer pair consisting of SEQ ID Nos. 32 and 33;
   wherein the composition further comprises probes consisting of SEQ ID Nos. 34 to 40 and 42 to 52, and the probes are fluorescent-labeled probes.

4. The composition according to claim 3, further comprising a hot start Taq DNA polymerase; reverse transcriptase; a primer pair represented by SEQ ID Nos. 15 and 16 for amplification of RNase P as internal control; and a probe having a nucleotide sequence of SEQ ID No. 41, as internal control.

5. A kit for simultaneous diagnosis of viral respiratory diseases, comprising the composition of claim 3.

6. A kit for simultaneous diagnosis of viral respiratory diseases,
   wherein the kit comprises 7 reaction containers, and each of the 7 reaction containers comprises a different primer set for simultaneous diagnosis of viral respiratory diseases
   selected from the following (a) to (g):
   (a) a primer set comprising a primer pair consisting of SEQ ID Nos. 1 and 2, a primer pair consisting of SEQ ID Nos. 3 and 4, and a primer pair consisting of SEQ ID Nos. 5 and 6; and probes consisting of SEQ ID Nos. 34, 35, and 36;
   (b) a primer set comprising a primer pair consisting of SEQ ID Nos. 7 and 8, a primer pair consisting of SEQ ID Nos. 9 and 10, and a primer pair consisting of SEQ ID Nos. 11 and 12; and probes consisting of SEQ ID Nos. 37, 38, and 39;
   (c) a primer set comprising a primer pair consisting of SEQ ID Nos. 13 and 14, and a primer pair consisting of SEQ ID Nos. 17 and 18; and probes consisting of SEQ ID Nos. 40 and 42;
   (d) a primer set comprising a primer pair consisting of SEQ ID Nos. 19 and 20, a primer pair consisting of SEQ ID Nos. 21 and 22, and a primer pair consisting of SEQ ID Nos. 23 and 24; and probes consisting of SEQ ID Nos. 43, 44 and 45; and
   (e) a primer set comprising a primer pair consisting of SEQ ID Nos. 25 and 26; a primer pair composed of a forward primer having a nucleotide sequence selected from the group consisting of SEQ ID Nos. 27 to 29 and a reverse primer having a nucleotide sequence selected from the group consisting of SEQ ID Nos. 30 and 31, and a primer pair consisting of SEQ ID Nos. 32 and 33; and probes consisting of SEQ ID Nos. 46 to 52;
   (f) a primer set comprising a primer pair consisting of SEQ ID Nos. 19 and 20, a primer pair consisting of SEQ ID Nos. 21 and 22, and a primer pair consisting of SEQ ID Nos. 32 and 33; and probes consisting of SEQ ID Nos. 43, 44, and 52; and
   (g) a primer set comprising a primer pair consisting of SEQ ID Nos. 25 and 26; a primer pair composed of a forward primer having a nucleotide sequence selected from the group consisting of SEQ ID Nos. 27 to 29 and a reverse primer having a nucleotide sequence selected from the group consisting of SEQ ID Nos. 30 and 31; and a primer pair consisting of SEQ ID Nos. 23 and 24; and probes consisting of SEQ ID Nos. 45 to 51;
   wherein the probes are fluorescent-labeled probes.

7. A kit for simultaneous diagnosis of viral respiratory diseases, comprising the composition of claim 4.

8. The method according to claim 1, which further comprises using probes consisting of SEQ ID Nos. 34 to 40 and 42 to 52.

9. The method according to claim 8, wherein the probes are fluorescent-labeled probes.

10. The method according to claim 1, wherein a primer pair having a nucleotide sequence of SEQ ID Nos. 1 and 2 specifically amplifies nucleoprotein (N) gene of corona virus 229E; a primer pair having a nucleotide sequence of SEQ ID Nos. 3 and 4 specifically amplifies nucleoprotein (N) gene of corona virus OC43; a primer pair having a nucleotide sequence of SEQ ID Nos. 5 and 6 specifically amplifies polyprotein (1a) gene of corona virus NL63; a primer pair having a nucleotide sequence of SEQ ID Nos. 7 and 8 specifically amplifies hemagglutinin-neuraminidase (HN) gene of parainfluenza virus 1; a primer pair having a nucleotide sequence of SEQ ID Nos. 9 and 10 specifically amplifies hemagglutinin-neuraminidase (HN) gene of parainfluenza virus 2; a primer pair having a nucleotide sequence of SEQ ID Nos. 11 and 12 specifically amplifies hemagglutinin-neuraminidase (HN) gene of parainfluenza virus 3; a primer pair having a nucleotide sequence of SEQ ID Nos. 13 and 14 specifically amplifies matrix protein (M) gene of influenza A virus; a primer pair having a nucleotide sequence of SEQ ID Nos. 17 and 18 specifically amplifies hemagglutinin (HA) gene of influenza B virus; a primer pair having a nucleotide sequence of SEQ ID Nos. 19 and 20 specifically amplifies fusion protein gene of respiratory syncytial virus A; a primer pair having a nucleotide sequence of SEQ ID Nos. 21 and 22 specifically amplifies fusion protein gene of respiratory syncytial virus B; a primer pair having a nucleotide sequence of SEQ ID Nos. 32 and 33 specifically amplifies nucleocapsid protein (NP) gene of boca virus; a primer pair having a nucleotide sequence of SEQ ID Nos. 25 and 26 specifically amplifies hexon protein gene of adenovirus; a primer pair having a nucleotide sequence selected from the group consisting of SEQ ID Nos. 27 to 31 specifically amplifies 5'UTR of rhino virus A, B, and C; and a primer pair having a nucleotide sequence of SEQ ID Nos. 23 and 24 specifically amplifies nucleoprotein (N) gene of metapneumovirus.

11. The method according to claim 1, which further comprises amplifying specifically the gene for RNase P by using a primer pair having a nucleotide sequence of SEQ ID Nos. 15 and 16, as internal control.

12. The method according to claim 1, which further comprises detecting the gene for RNase P by using a probe having a nucleotide sequence of SEQ ID No. 41, as internal control.

13. The composition according to claim 3, comprising:
(a) a primer set comprising a primer pair consisting of SEQ ID Nos. 1 and 2, a primer pair consisting of SEQ ID Nos. 3 and 4, and a primer pair consisting of SEQ ID Nos. 5 and 6; and probes consisting of SEQ ID Nos. 34, 35, and 36;
(b) a primer set comprising a primer pair consisting of SEQ ID Nos. 7 and 8, a primer pair consisting of SEQ ID Nos. 9 and 10, and a primer pair consisting of SEQ ID Nos. 11 and 12; and probes consisting of SEQ ID Nos. 37, 38, and 39;
(c) a primer set comprising a primer pair consisting of SEQ ID Nos. 13 and 14, and a primer pair consisting of SEQ ID Nos. 17 and 18; and probes consisting of SEQ ID Nos. 40 and 42;
(d) a primer set comprising a primer pair consisting of SEQ ID Nos. 19 and 20, a primer pair consisting of SEQ ID Nos. 21 and 22, and a primer pair consisting of SEQ ID Nos. 23 and 24; and a primer pair consisting of SEQ ID Nos. 23 and 24; and probes consisting of SEQ ID Nos. 43, 44 and 45;
(e) a primer set comprising a primer pair consisting of SEQ ID Nos. 25 and 26; a primer pair composed of a forward primer having a nucleotide sequence selected from the group consisting of SEQ ID Nos. 27 to 29 and a reverse primer having a nucleotide sequence selected from the group consisting of SEQ ID Nos. 30 and 31, and a primer pair consisting of SEQ ID Nos. 32 and 33; and probes consisting of SEQ ID Nos. 46 to 52;
(f) a primer set comprising a primer pair consisting of SEQ ID Nos. 19 and 20, a primer pair consisting of SEQ ID Nos. 21 and 22, and a primer pair consisting of SEQ ID Nos. 32 and 33; and probes consisting of SEQ ID Nos. 43, 44, and 52; and
(g) a primer set comprising a primer pair consisting of SEQ ID Nos. 25 and 26; a primer pair composed of a forward primer having a nucleotide sequence selected from the group consisting of SEQ ID Nos. 27 to 29 and a reverse primer having a nucleotide sequence selected from the group consisting of SEQ ID Nos. 30 and 31; and a primer pair consisting of SEQ ID Nos. 23 and 24; and probes consisting of SEQ ID Nos.45 to 51;
wherein the probes are fluorescent-labeled probes.

* * * * *